US010258287B2

(12) United States Patent
Heindl et al.

(10) Patent No.: US 10,258,287 B2
(45) Date of Patent: Apr. 16, 2019

(54) POSITIONING DEVICE FOR A MEDICAL FIELD GENERATOR

(71) Applicant: Brainlab AG, Munich (DE)

(72) Inventors: Nadja Heindl, Jettenbach (DE); Patra Mladenovic, Karlsfeld (DE); Marta Gonzalez, Munich (DE); Gerd Barta, Neubiberg (DE)

(73) Assignee: Brainlab AG, Munich (DE)

(*) Notice: Subject to any disclaimer, the term of this patent is extended or adjusted under 35 U.S.C. 154(b) by 140 days.

(21) Appl. No.: 14/439,738

(22) PCT Filed: Oct. 31, 2012

(86) PCT No.: PCT/EP2012/071622
§ 371 (c)(1),
(2) Date: Apr. 30, 2015

(87) PCT Pub. No.: WO2014/067576
PCT Pub. Date: May 8, 2014

(65) Prior Publication Data
US 2015/0297303 A1 Oct. 22, 2015

(51) Int. Cl.
*A61B 5/00* (2006.01)
*A61B 6/04* (2006.01)
(Continued)

(52) U.S. Cl.
CPC .............. *A61B 5/704* (2013.01); *A61B 5/062* (2013.01); *A61B 5/6891* (2013.01); *A61B 6/04* (2013.01);
(Continued)

(58) Field of Classification Search
CPC ......... A61B 34/20; A61B 90/50; A61B 5/062; A61B 5/704
See application file for complete search history.

(56) References Cited

U.S. PATENT DOCUMENTS 5,337,760 A * 8/1994 Nichols ................ A61B 6/0421
128/DIG. 15
6,138,304 A * 10/2000 Lipsky .................. A61G 13/12
5/621
(Continued)

FOREIGN PATENT DOCUMENTS

EP  1 570 781   9/2005
EP  2 100 557   9/2009
(Continued)

OTHER PUBLICATIONS

International Search Report and Written Opinion for International Application No. PCT/EP2012/071622 dated Oct. 31, 2012 (4 pages).

*Primary Examiner* — Katherine L Fernandez
*Assistant Examiner* — Yi-Shan Yang
(74) *Attorney, Agent, or Firm* — Tucker Ellis, LLP

(57) ABSTRACT

A positioning device for a medical field generator includes a base member, an adaptor connected with the base member and configured to support a field generator, and a fixing member allowing the positioning device to be fixed to an associated operating table. The base member includes at least one contacting section and is configured to contact an upper surface of an operating table. The adaptor is configured to prevent the field generator from being positioned at less than a predetermined distance from the operating table. A method positions a medical field generator. The field generator is attached with the positioning device. A base member of the positioning device, with the field generator attached to it, is positioned on the upper surface of the operating table and beneath a part of a head of a patient lying on the operating table. The positioning device is fixedly attached with the operating table.

21 Claims, 5 Drawing Sheets

(51) Int. Cl.
  *A61B 5/06* (2006.01)
  *A61B 34/20* (2016.01)
  *A61B 90/50* (2016.01)

(52) U.S. Cl.
  CPC .............. *A61B 34/20* (2016.02); *A61B 90/50* (2016.02); *A61B 2034/2051* (2016.02); *A61B 2034/2072* (2016.02)

(56) References Cited

U.S. PATENT DOCUMENTS

| | | | | |
|---|---|---|---|---|
| 7,551,432 B1* | 6/2009 | Bockheim | .......... | F16M 11/2014 361/679.07 |
| 8,479,743 B2* | 7/2013 | Moyers | ................ | A61N 5/1049 128/846 |
| 2004/0199072 A1 | 10/2004 | Sprouse | | |
| 2006/0016006 A1* | 1/2006 | Whitmore, III | ...... | A61B 6/0442 5/601 |
| 2006/0198978 A1* | 9/2006 | Antonini | ................ | B32B 33/00 428/41.8 |
| 2007/0039621 A1* | 2/2007 | Moyers | ................ | A61N 5/1049 128/857 |
| 2008/0026892 A1* | 1/2008 | Asamarai | ............ | F16M 11/046 474/84 |
| 2009/0229732 A1* | 9/2009 | Determan | ................ | B32B 7/12 156/60 |
| 2009/0247993 A1* | 10/2009 | Kirschenman | .... | A61M 25/0147 606/1 |
| 2010/0008475 A1* | 1/2010 | Maschke | .................. | A61B 5/06 378/209 |
| 2011/0054297 A1* | 3/2011 | Bulitta | ..................... | A61B 5/06 600/407 |
| 2012/0119040 A1* | 5/2012 | Ergun | .................... | A47B 21/02 248/126 |
| 2014/0350387 A1* | 11/2014 | Siewerdsen | .......... | G01R 33/028 600/424 |

FOREIGN PATENT DOCUMENTS

| | | | | |
|---|---|---|---|---|
| EP | 1570781 B1 * | 9/2009 | ............... | A61B 5/06 |
| GB | 2113502 | 8/1983 | | |

\* cited by examiner

POSITIONING DEVICE FOR A MEDICAL FIELD GENERATOR

RELATED APPLICATION DATA

This application is a national phase application of International Application No. PCT/EP2012/071622 filed Oct. 31, 2012 and published in the English language.

The present invention relates to a positioning device for a medical field generator which holds the field generator in a predetermined position relative to the patient and to an operating table. The present invention relates also to a method for positioning such a medical field generator.

In modern surgery, in particular neurosurgery, instruments and devices are used which can be localised and tracked in three dimensions by means of a medical tracking system. If an EM tracking system is used, a magnetic field generated by a medical field generator allows instruments to be localised and tracked within the magnetic field. However, the magnetic field emitted by the field generator varies over the measurement volume, such that the accuracy of the electromagnetic tracking system is spatially dependent. The usable tracking volume usually starts at a certain distance from the field generator and transitions into a region of maximum accuracy, beyond which the accuracy then decreases again as the distance from the field generator continues to increase. In order to achieve the maximum possible accuracy during a procedure, the sensors and the region of interest on or in the patient must be within the region of maximum accuracy.

Conductive or ferromagnetic material which is exposed to the changing magnetic field created by the field generator will also cause field distortion which will affect the tracking accuracy. Since the operating table may contain metal components, accuracy could be impaired if the field generator is too close to the operating table. Therefore, a minimum distance between the field generator and the operating table should be maintained.

In order to maintain a suitable position of the field generator relative to the region of interest, for example the patient's head, and to the operating table, articulated arms are used which are connected to the operating table and hold the field generator in a predetermined position. Although this enables the user to optimise the OR setup in accordance with the needs of the individual patient and clinical case, the setup flexibility provided by an articulated arm could also lead to unsatisfactory system accuracy if the field generator is held in an unsuitable position, for example too close to the operating table or too far away from it and/or too close to the region of interest. Such an articulated arm also has a significant weight of its own, and setting it up is involved and time-consuming. Also, since the weight of the field generator is supported exclusively by the articulated arm, misalignment caused by unintended strikes or jolts against the field generator or the articulated arm cannot be precluded. If the arm joint(s) become(s) loose, the arm could fold or pivot in an unexpected way, harming the patient and/or user and/or at least increasing navigation inaccuracy.

It is an object of the present invention to overcome at least one of the aforementioned drawbacks of prior-art field generator holders.

The positioning device in accordance with the invention comprises:
a base member which comprises at least one contacting section and is configured to contact the upper surface of an operating table;
an adaptor which is connected to the base member and configured to support the field generator; and
a fixing element which allow(s) the positioning device to be fixed to an operating table,
wherein the adaptor is configured to prevent the field generator from being positioned at less than a predetermined distance from the operating table.

In other words, the base member of the positioning device is placed onto an operating table and fixed to the operating table via fixing means, wherein by means of its adaptor, the positioning device holds the field generator such that the distance between the positioned field generator and the operating table cannot fall below a predetermined limit as long as the field generator is held by means of the adaptor of the positioning device. Since the base member of the positioning device is configured to contact the upper surface of the operating table, the adaptor also prevents the field generator from being positioned at less than a predetermined distance from the base member.

The field generator cannot therefore be positioned too close to the operating table, which may contain metal parts which would influence the magnetic field and therefore also the accuracy of the medical tracking system. This could be achieved by an adaptor which is placed at least partially between the field generator and the base member and forms an obstacle which blocks any positional approach by the field generator towards the base member/operating table which would violate the predetermined limit. The fixing means can comprise any means suitable for fixing the position of the positioning device relative to the operating table. To avoid field distortions caused by the positioning device itself, the positioning device may be made entirely of non-metal material, preferably plastic material.

In accordance with a further embodiment of the present invention, the adaptor is configured to unmodifiably maintain the position of the field generator relative to the base member.

Such an adaptor forms a rigid and invariant connection between the base member and the field generator, wherein the position—specifically, the distance—between the field generator and the base member can be predetermined for a specific type of field generator and its magnetic field. Since the position of the field generator relative to the base member is invariant, the position of the field generator relative to the operating table can only be altered by moving the base member relative to the operating table. This also helps to prevent the position of the field generator from being unintentionally altered.

In accordance with preferred further embodiment of the present invention, the adaptor and the base member form an integral unit. An integrally formed positioning device is not only inexpensive to produce and easy to keep clean, but any adjustments which could lead to an unsuitable position of the field generator are also then prevented.

Although a positioning device which unmodifiably maintains the position of the field generator relative to the base member is conceivable, it is also conceivable for a positioning device to be provided with an adaptor which allows the field generator to be positionally adjusted with respect to the base member, in particular in a direction which is substantially perpendicular to a plane defined by the at least one contacting section, and specifically in this direction only. In other words, the adaptor is configured to allow the field generator to be positionally adjusted with respect to the base member as long as the distance between the field generator and the operating table does not fall below a predetermined limit.

In general, the positioning device can be adapted to allow different types of field generators—which can generate magnetic fields of different strengths, volumes and/or shapes—to be attached. An adjustable adaptor would then be beneficial, since a field generator which generates a small magnetic field can be positioned closer to the operating table than a field generator which generates a large magnetic field, without running the risk of distorting the magnetic field. Such an adaptor may comprise means which indicate to the user the minimum distance for a specific type of field generator and guide the user in placing the field generator at the correct distance for maximum accuracy. Means could also be provided which prevent a specific type of field generator from being positioned at less than a minimum distance which is predetermined for said type of field generator, whereas placing a different field generator, which for example generates a smaller magnetic field, closer to the base member and therefore to the operating table is allowed. The adaptor could also be configured to only allow the field generator to be positionally adjusted prior to use, so that the field generator is prevented from being positionally adjusted unintentionally during surgery.

Although an adaptor which is integrally formed with the base member is preferred, an adaptor which is detachably and reproducibly mounted on the base member and/or field generator, in particular by means of screw connections, is also conceivable. It would then be possible to use the same base member for different types of adaptors which are configured to fit different types of field generators and in particular configured to only fit a field generator for which the specific adaptor is designed. As an alternative to a screw connection, any suitable detachable connection is conceivable for mounting the adaptor to the base member and/or field generator.

An adaptor which is connected to the field generator by means of a positive fit is also conceivable. Such an adaptor can at least partially encompass the field generator, thus further simplifying the connection between the positioning device and the field generator.

In accordance with another embodiment of the present invention, the base member is configured to be able to be ergonomically placed between the upper surface of an operating table and a part of the body, in particular a patient's head lying on the operating table, wherein the base member is specifically shaped like a tray. If the base member is ergonomically formed and can be placed between the operating table and the patient, the weight of the patient will help to maintain the position of the field generator by pressing the base member onto the upper surface of the operating table. Means which provide an anti-slip surface on the underside of the base member and which contact the upper surface of the operating table can also help to maintain the position of the positioning device on the upper surface of the operating table. Such anti-slip means can be provided irrespective of whether or not the base member is placed between the patient and the operating table.

A base member which is designed to be positioned between the patient and the operating table can also comprise an area where a part of the patient's body can rest, for example a headrest area, provided on the upper surface of the base member, and an adaptor area which is in particular positioned adjacent to the headrest area on the upper surface of the base member, wherein the adaptor is formed or mounted on the base member. Such a base member can in particular be used when the field generator is to be positioned close to the patient's head, for example for neurosurgery.

The headrest area can comprise means which allow the part of the patient's body—for example, the patient's head—to be ergonomically placed or can at least form a seat for known head-supporting means which are provided separately from the positioning device for the field generator.

In accordance with a further embodiment of the present invention, the positioning device—in particular, the base member—comprises at least one positioning aid which is configured to help properly position the positioning device on an operating table, specifically by means of the shape of the base member itself. Properly placing the field generator with respect to the operating table is already ensured by the fact that the adaptor maintains a predetermined distance between the field generator and the operating table. However, the position of the field generator could still be altered in a plane which is parallel to the surface of the operating table. Therefore, it would be beneficial to guide the user in such a way that a suitable position of the field generator with respect to the patient's region of interest can also be easily found. The positioning device—or more specifically, the base member—can correspondingly comprise means which can be aligned with corresponding features of the operating table, such as for example correspondingly formed edges or cutouts formed on the base member which can be aligned with corresponding structures on the operating table. The positioning device—more specifically, the base member—can also comprise means which indicate a suitable position for a part of a patient's body, for example a patient's head. The positioning device can also include such features for different positions of the positioning device, such that the field generator can be repositioned as desired during surgery, after the fixation of the positioning device to the operating table has been released. A base member which is formed to be symmetrical, in particular rotationally symmetrical or mirror-symmetrical, can be advantageous in this respect.

The fixing means of the positioning device can be or comprise at least one interface in order to allow fixation means to engage with the positioning device, in particular by means of a frictional fit and/or a positive fit, wherein any type of fixation means which is suitable for fixing the positioning device to the operating table is conceivable, such as for example hook-and-loop fasteners (Velcro® straps) which engage with the fixing means of the positioning device and are placed around the operating table.

At least one through-hole in the base member can form the at least one interface. The positioning device—in particular, the base member—in accordance with the invention can comprise a medical head-holder or a mounting interface for a medical head-holder for fixing a patient's head to the positioning device and operating table, respectively. Whereas a headrest area formed by the base member would allow at least a small movement of the patient's head, a medical head-holder which is connected to the positioning device prevents any movement of the patient's head, thereby providing an invariant position of the head within the magnetic field.

Another aspect of the present invention relates to a method for positioning a medical field generator, comprising the following steps:
 providing a medical field generator (2) and a positioning device (1) as described above;
 attaching the field generator (2) to the positioning device (1);
 positioning a base member (3) of the positioning device (1), with the field generator (2) attached to it, on the upper surface of an operating table and beneath a part of a patient's body, in particular the head of a patient lying on the operating table;
 fixing the positioning device (1) to the operating table.

The method in accordance with the invention can also comprise at least one of the following steps:
- obtaining information about a proper, in particular optimum, positional placement of the field generator (2) with respect to the part of the patient's body and/or the operating table;
- adjusting the adaptor (4) such that the distance between the operating table and the field generator (2) fulfils the requirements for a properly placed field generator (2);
- positioning the base member (3) on the upper surface of the operating table, such that the positional arrangement of the part of the patient's body and the field generator (2) fulfils the requirements for a properly placed field generator (2);
- positioning and fixing the positioning device (1) to the operating table in a position which differs from a preceding position.

The invention will now be described in more detail by referring to particular embodiments and the attached figures. It should be noted that each of the features of the present invention as referred to here can be implemented separately or in any expedient combination.

Figure 1:
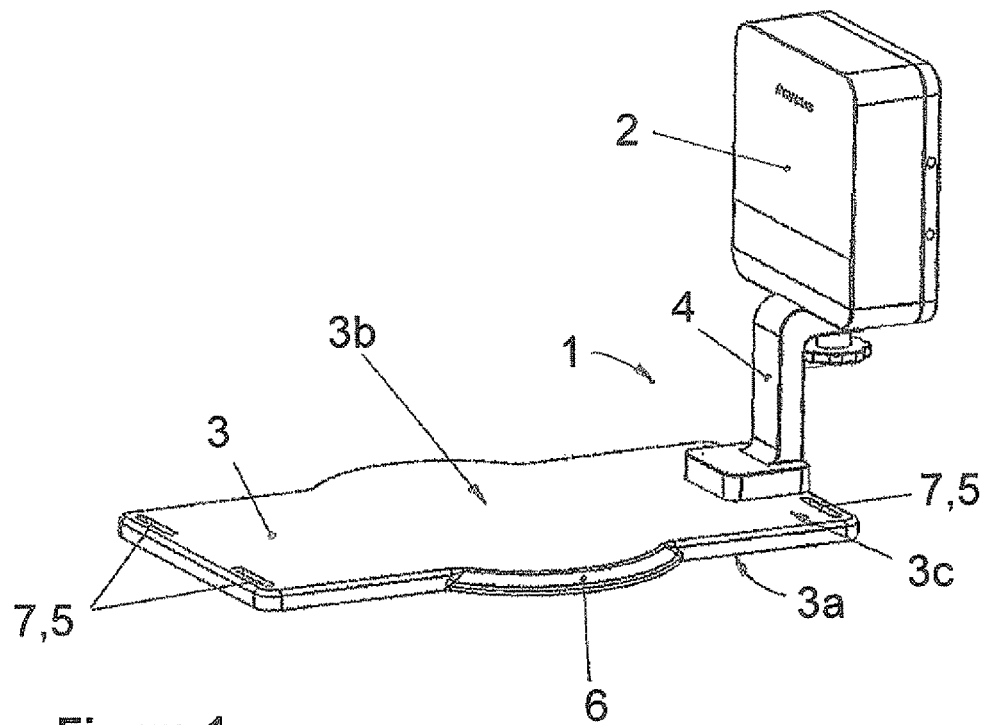
FIG. 1 shows an embodiment of the positioning device in accordance with the invention, with a medical field generator attached to the adaptor.
Figures 3, 4:
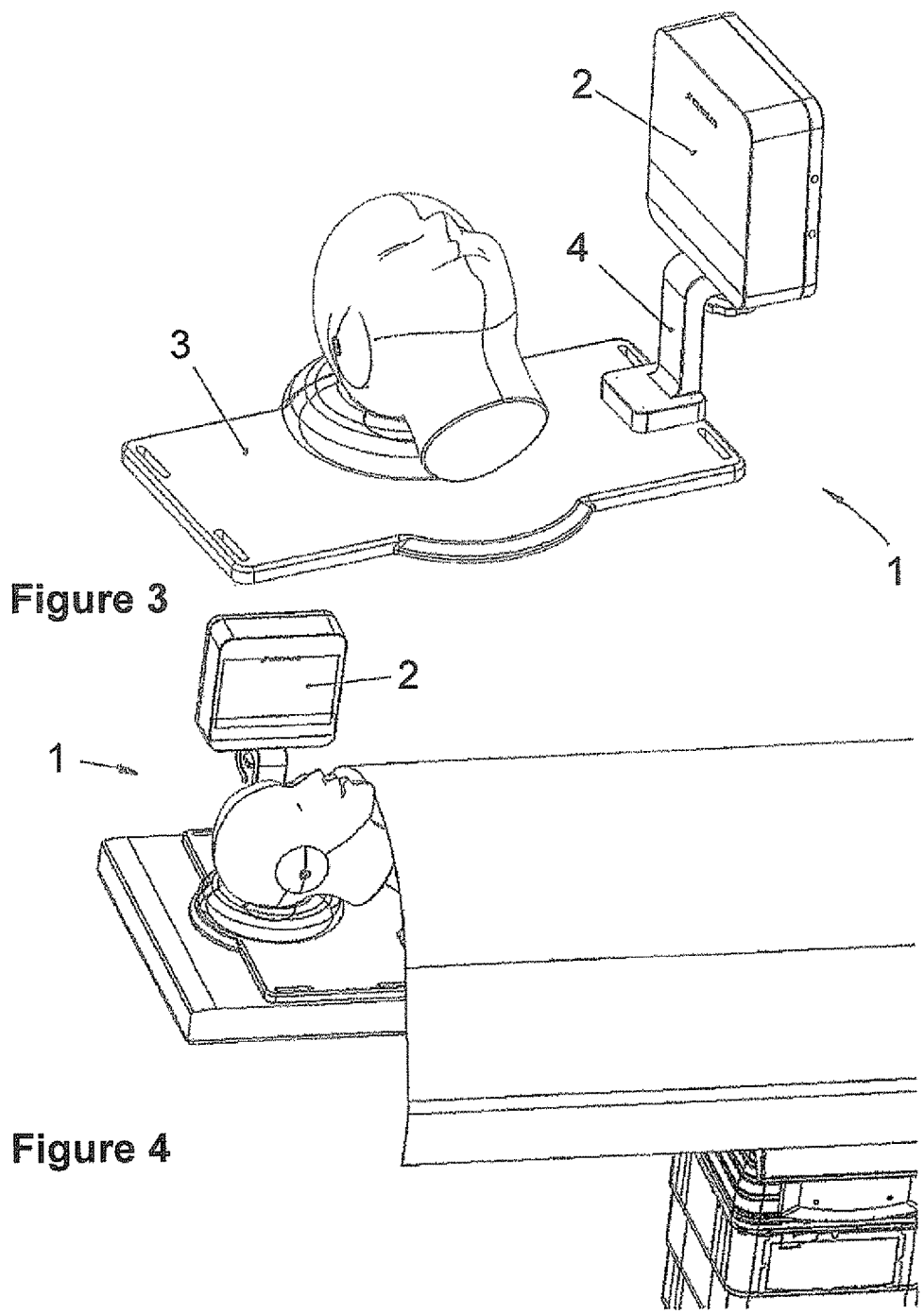
FIG. 3 shows the positioning device of FIGS. 1 and 2, with a human patient's head placed on the positioning device.
FIG. 4 shows the positioning device of FIGS. 1 to 3 on an operating table and with a patient's head placed on it.

A first embodiment of the positioning device in accordance with the invention is shown in FIG. 1, wherein the positioning device 1 comprises a flat base member 3 featuring a lower side 3a which is configured to contact the upper surface of an operating table, and an upper surface 3b, 3c for placing a patient's head and an adaptor 4, respectively, wherein the adaptor 4 holds a medical field generator 2. The substantially rectangular base member 3 comprises two projections 6 which together describe a circle, thereby indicating the proper placement of a patient's head, i.e. for example at the centre of the circle. The projections 6 thus form a positioning aid for positioning the field generator relative to a patient's head. The short edges of the substantially rectangular base member 3 form another positioning aid, since they fit the table's side edges, as can be seen in FIG. 4. Away from the headrest area and adjacent to the side edges of the base member 3, through-holes are formed in the base member 3 which form an interface 5, 7 in order to allow fixation means to engage with the base member 3.

Figure 7:
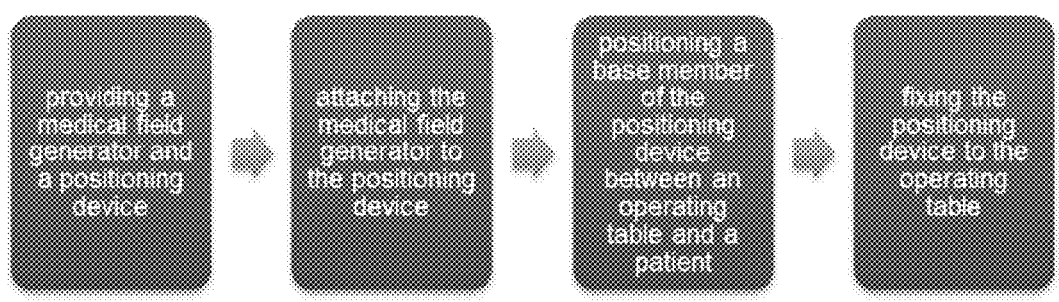
FIG. 7 shows a flow diagram of a method in accordance with the invention.

A representative flow diagram of a method according to an embodiment of the present invention is shown in FIG. 7.

Figure 2:
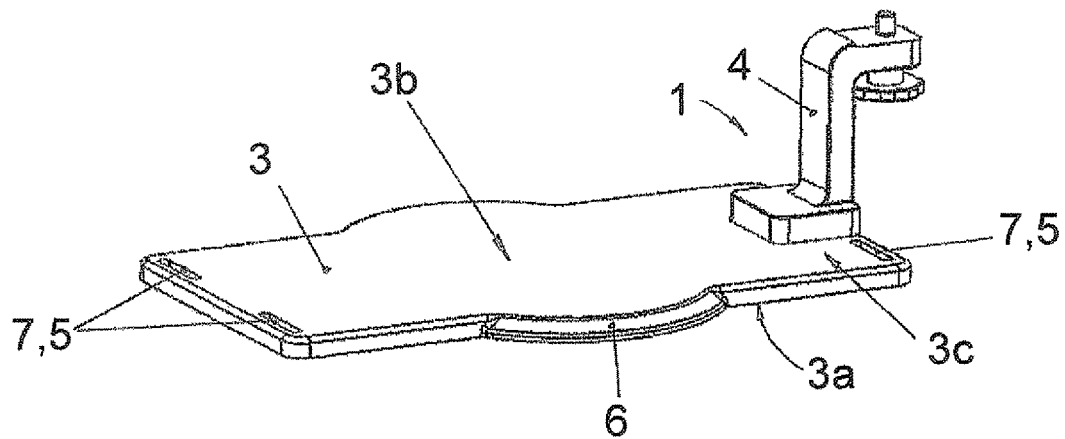
FIG. 2 shows the positioning device of FIG. 1, without the medical field generator.

As can be seen in FIG. 2, the adaptor 4 comprises a screw which is connected to a hand wheel and constitutes a threaded interface of the field generator 2. The adaptor 4 also comprises an upper edge which fits a lower edge of the field generator housing, thereby only allowing a predetermined position of the field generator 2 with respect to the base member 3 and preventing any rotational movement of the field generator 2 around the rotational axis of the hand wheel.

As can be seen in FIG. 3, the patient's head can be placed onto the base member 3 with the aid of a supporting structure—in this case, in the form of a gel-filled, doughnut-shaped cushion. The circularly shaped protrusions 6 can again aid in properly placing the gel-filled cushion on the base member 3.

Figure 5:
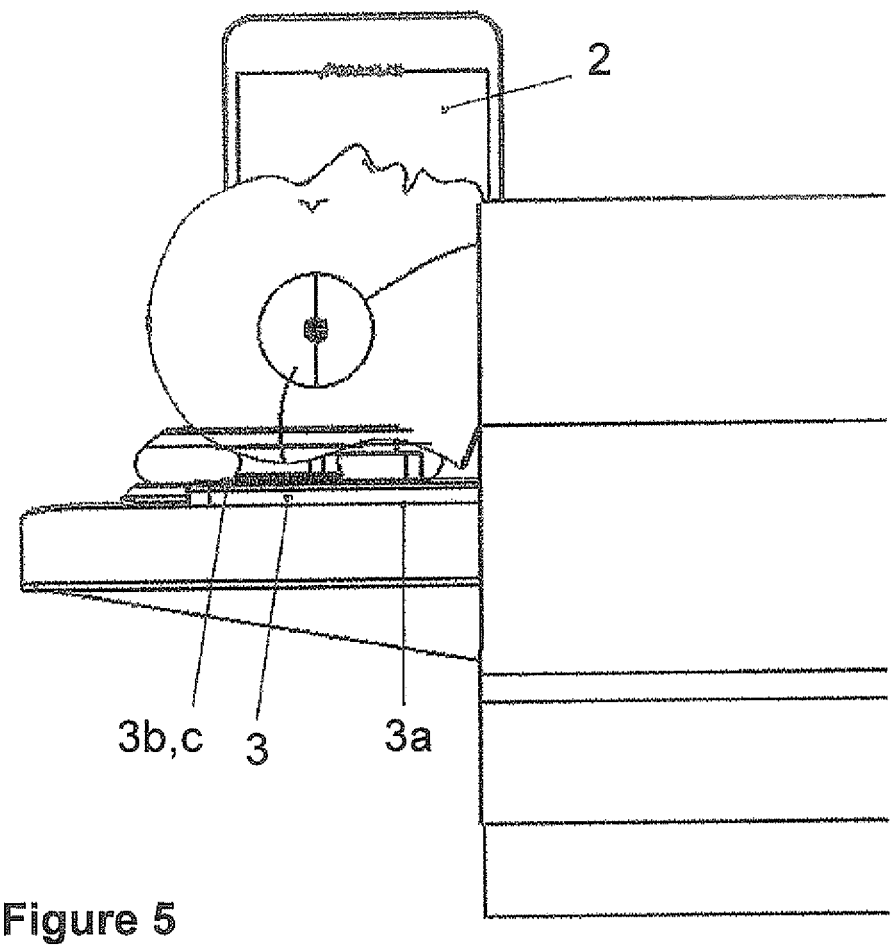
FIG. 5 is a side view of the positioning device shown in FIG. 4.

As already described above and shown in FIGS. 4 and 5, the edges of the base member 3 can aid in properly positioning it on the operating table. Since the base member 3 is formed to be mirror-symmetrical, the positioning device 1 together with the field generator 2 can be turned through 180 degrees so as to allow the left side of the head to also be operated on, wherein the side edges and the circularly shaped protrusions 6 can again aid in properly re-positioning the positioning device 1.

Figure 6:
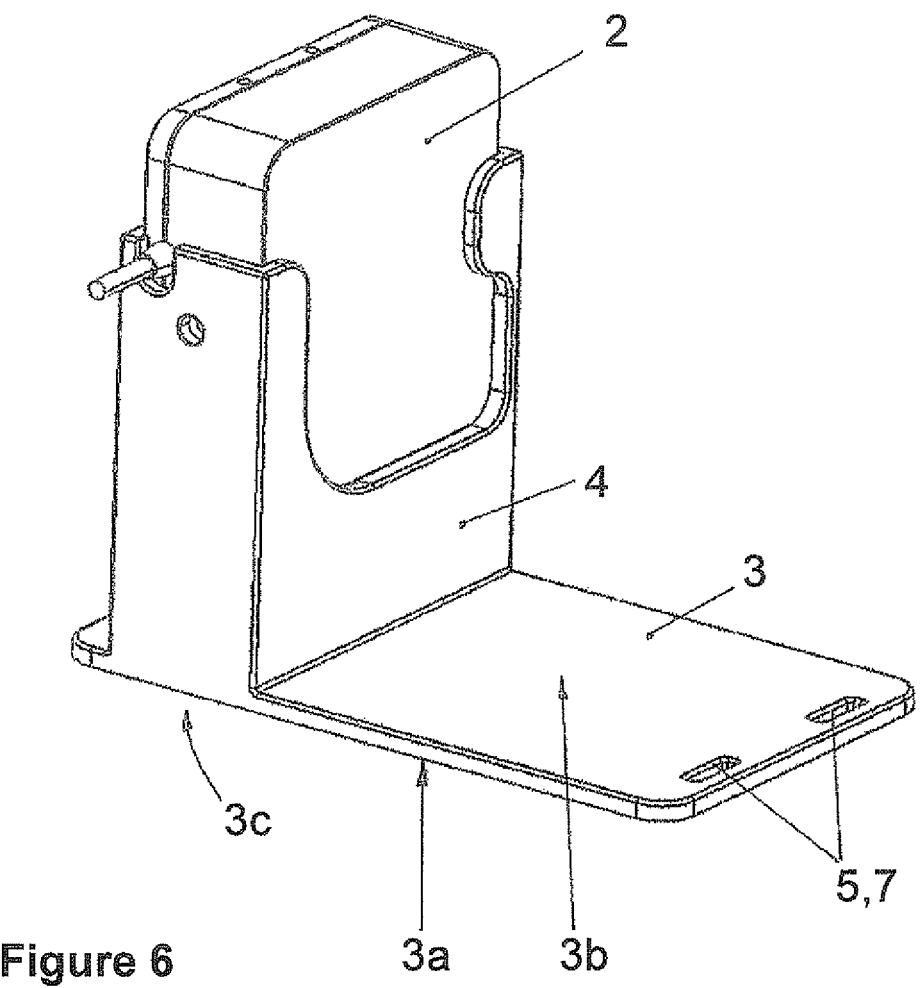
FIG. 6 shows another embodiment of the positioning device in accordance with the invention.

The embodiment shown in FIG. 6 differs from the embodiment described in the preceding figures and the corresponding text of the description in that the adaptor 4 is integrally formed with the base member 3 and partially encompasses the field generator 2.

The adaptor 4 of any of the embodiments described above is positioned at least partially between the base member 3 and the field generator 2 and therefore prevents the field generator 2 from being positioned at less than a predetermined distance from the operating table, namely the vertical extension of the adaptor 4 between the operating table and the field generator 2.

The invention claimed is:

1. A positioning device for an associated medical field generator, the positioning device comprising:
    a tray-shaped base member comprising
        a bottom surface adapted for contacting an upper surface of an associated operating table and
        a top surface adapted for a head of an associated patient lying on the associated operating table to rest when the tray-shaped base member is selectively disposed between the upper surface of the associated operating table and the head of the associated patient,
        wherein the base member is sized large enough for the head of the associated patient to be placed onto the top surface of the base member,
        wherein the base member is configured to be secured in place on the upper surface of the associated operating table by weight of the head of the associated patient pressing the base member onto the upper surface of the associated operating table when the base member is disposed between the upper surface of the associated operating table and the head of the associated patient,
        wherein the base member has a substantially rectangular shape comprising edges and two projections defining a circle,
            wherein the two projections are on opposite edges of the base member,
        wherein the edges form a first positioning aid for aiding a positioning of the base member relative to the associated operating table; and
    an adaptor protruding from the base member, the adaptor coupling the associated medical field generator with the base member in a spatially invariant manner to maintain both a location and an orientation of the associated medical field generator relative to the base member,
        wherein the adaptor blocks a positional approach of the associated medical field generator towards the base member beyond a predetermined distance between the associated medical field generator and the base member, wherein the two projections of the base member defining the circle form a second positioning aid for aiding a positioning of the head of the associated patient relative to the associated medical field generator coupled with the base member by the adapter.

2. The positioning device according to claim 1, wherein the adaptor unmodifiably maintains the position of the associated medical field generator relative to the base member.

3. The positioning device according to claim 1, wherein the adaptor and the base member form an integral unit.

4. The positioning device according to claim 1, wherein the circle has a center, the center of the circle forming the second positioning aid for aiding in the positioning of the head of the associated patient relative to the associated medical field generator.

5. The positioning device according to claim 1, further comprising one or more screw connections, wherein the adaptor is detachably and reproducibly mounted on the base member and/or the associated medical field generator by the one or more screw connections.

6. The positioning device according to claim 1, wherein the base member is flat.

7. The positioning device according to claim 6, wherein the base member comprises a headrest area and an adaptor area, the headrest area being provided on the upper surface of the base member, and the adaptor area being positioned adjacent to the headrest area on the upper surface of the base member, wherein the adaptor is formed or mounted on the base member.

8. The positioning device according to claim 1, further comprising:
one or more through-holes defined in the base member, the one or more through-holes forming an interface adapted to selectively engage an associated fixing element configured to fix the positioning device relative to the associated operating table.

9. The positioning device according to claim 1, wherein the tray-shaped base member has a rotationally symmetrical or a mirror symmetrical shape.

10. The positioning device according to claim 1, further comprising a fixing element which allows the positioning device to be fixed to the associated operating table, the fixing element comprising at least one interface that allows the fixing element to engage with the positioning device.

11. The positioning device according to claim 10, wherein the at least one interface comprises at least one through-hole defined by the base member.

12. The positioning device according to claim 1, further comprising:
a medical head-holder or a mounting interface for a medical head-holder that is adapted to fix the head of the associated patient to the positioning device and the associated operating table, respectively.

13. A method comprising:
providing an associated medical field generator and a positioning device comprising:
a tray-shaped base member which comprises
a bottom surface for contacting an upper surface of an associated operating table and
a top surface adapted for a head of an associated patient lying on the associated operating table to rest,
wherein the base member is configured to be placed between the upper surface of the associated operating table and the head of the associated patient,
wherein the base member is sized large enough for the head of the associated patient to be placed onto the top surface of the base member to secure the base member in place on the upper surface of the associated operating table by pressing the base member onto the upper surface of the associated operating table by the weight of the head of the associated patient,
wherein the base member has a substantially rectangular shape comprising edges and two projections defining a circle,
wherein the two projections are on opposite edges of the base member,
wherein the edges form a first positioning aid for aiding a positioning of the base member relative to the associated operating table; and
an adaptor protruding from the base member, the adaptor coupling the associated medical field generator with the base member in a spatially invariant manner thereby maintaining both a location and an orientation of the associated medical field generator relative to the base member,
wherein the adaptor blocks a positional approach of the associated medical field generator towards the base member beyond a predetermined distance between the associated medical field generator and the base member,
wherein the two projections of the base member defining the circle form a second positioning aid for aiding a positioning of the head of the associated patient relative to the associated medical field generator coupled with the base member by the adapter;
attaching the associated medical field generator to the positioning device; and
positioning the base member of the positioning device, with the associated medical field generator attached to it between an upper surface of the associated operating table and a body part of the associated patient lying on the associated operating table.

14. The method according to claim 13, further comprising at least one of the following steps:
obtaining information about a placement of the associated medical field generator with respect to the part of the body of the associated patient and/or the associated operating table;
adjusting the adaptor such that the distance between the associated operating table and the associated medical field generator fulfills requirements for the placement of the associated medical field generator;
positioning the base member on the upper surface of the associated operating table, such that the positional arrangement of the part of the body of the associated patent and the associated medical field generator fulfills the requirements for the placement of the associated medical field generator; and/or positioning and fixing the positioning device to the associated operating table in a position which differs from a preceding position.

15. The positioning device according to claim 1, wherein:
the bottom surface of the tray-shaped base member comprises an anti-slip surface configured to contact the upper surface of the associated operating table, the anti-slip surface maintaining a relative position between the base member and the upper surface of the associated operating table fixed.

16. A positioning device for positioning an associated medical field generator relative to an associated an upper surface of an associated operating table, the positioning device comprising:
  a tray-shaped base member comprising opposite top and bottom surfaces,
    the bottom surface being configured to contact the upper surface of the associated operating table and
    the top surface being configured to support a head of an associated patient lying on the associated operating table,
    the tray-shaped base member being sized large enough for the head of the associated patient to be placed onto the top surface of the tray-shaped base member with the associated patient lying on the associated operating table,
      wherein the base member has a substantially rectangular shape comprising edges and two projections defining a circle,
        wherein the two projections are on opposite edges of the base member,
        wherein the edges form a first positioning aid for aiding a positioning of the base member relative to the associated operating table;
  a fixing element configured to fix the tray-shaped base member to the associated operating table; and
  an adaptor protruding from the base member,
    the adaptor coupling the associated medical field generator with the base member in a spatially invariant manner thereby maintaining both a location and an orientation of the associated medical field generator relative to the base member fixed,
    the adaptor blocking a positional approach of the associated medical field generator towards the base member beyond a predetermined distance between the associated medical field generator and the base member,
    wherein the two projections of the base member defining the circle form a second positioning aid for aiding a positioning of the head of the associated patient relative to the associated medical field generator coupled with the base member by the adapter.

17. The positioning device according to claim 16, wherein the tray-shaped base member has a rotationally symmetrical or a mirror symmetrical shape.

18. The positioning device according to claim 16, wherein:
  the bottom surface of the tray-shaped base member comprises an anti-slip surface configured to contact the upper surface of the associated operating table, the anti-slip surface maintaining fixed a relative position between the base member and the upper surface of the associated operating table.

19. The positioning device according to claim 16, wherein:
  the fixing element comprises at least one interface that allows an associated fixation element to engage with the positioning device.

20. The positioning device according to claim 19, wherein:
  the at least one interface of the fixing element comprises at least one through-hole defined by the tray-shaped base member, the at least one through-hole being adapted to receive the associated fixation element therethrough.

21. The positioning device according to claim 16, wherein: the base member and the adaptor form an integral unit made entirely of non-metal material to reduce distortion of a field generated by the associated medical field generator.

* * * * *